United States Patent [19]

Kuypers et al.

[11] Patent Number: 5,000,180

[45] Date of Patent: Mar. 19, 1991

[54] POLAROGRAPHIC-AMPEROMETRIC THREE-ELECTRODE SENSOR

[75] Inventors: Martinus H. Kuypers, Riethoven; Gerardus F. J. Steeghs, Geldrop, both of Netherlands

[73] Assignee: Biomedical Systems Inc., Pittsburgh, Pa.

[21] Appl. No.: 386,759

[22] Filed: Jul. 31, 1989

[30] Foreign Application Priority Data

Aug. 3, 1988 [EP] European Pat. Off. .......... 88112641

[51] Int. Cl.$^5$ ............................................ G01N 27/31
[52] U.S. Cl. ................................... 128/635; 204/403; 204/412
[58] Field of Search ................. 204/412, 403; 128/635

[56] References Cited

U.S. PATENT DOCUMENTS

| | | | |
|---|---|---|---|
| 4,492,622 | 1/1985 | Kuypers | 204/403 |
| 4,538,617 | 9/1985 | Jensen | 128/635 |
| 4,624,261 | 11/1986 | Hölscher | 128/635 |
| 4,681,115 | 7/1987 | Hölscher | 128/635 |
| 4,685,465 | 8/1987 | Kiltgaard et al. | 128/635 |

OTHER PUBLICATIONS

"Polarographic Oxygen Sensor", CRC Press, Inc. by I. Fatt, pp. 1-7.
Fabrication of Voltammetric Sensors With Planar Techniques, Conference paper "International Conference on Solid-State Sensors and Atuators," Transducers '85, IEEE Transactions, pp. 344-345.

*Primary Examiner*—G. L. Kaplan
*Attorney, Agent, or Firm*—McGlew & Tuttle

[57] ABSTRACT

For a potentiostatically operable, polarographic-amperometric sensor, in particular for biomedical use, wherein a working electrode (5) and a reference electrode (4) are covered by an electrolyte layer (9) which is separated from the medium to be measured by a semipermeable membrane (8), the invention proposes to provide the counter electrode (6) in the form of an external electrode which—for example—can be an outer metal coating surrounding the sensor chip (2) in a three electrode system fabricated as micro-sensor with the integrated technique, and which can be made—for example—of a stainless steel material or of a conductive plastics material.

8 Claims, 3 Drawing Sheets

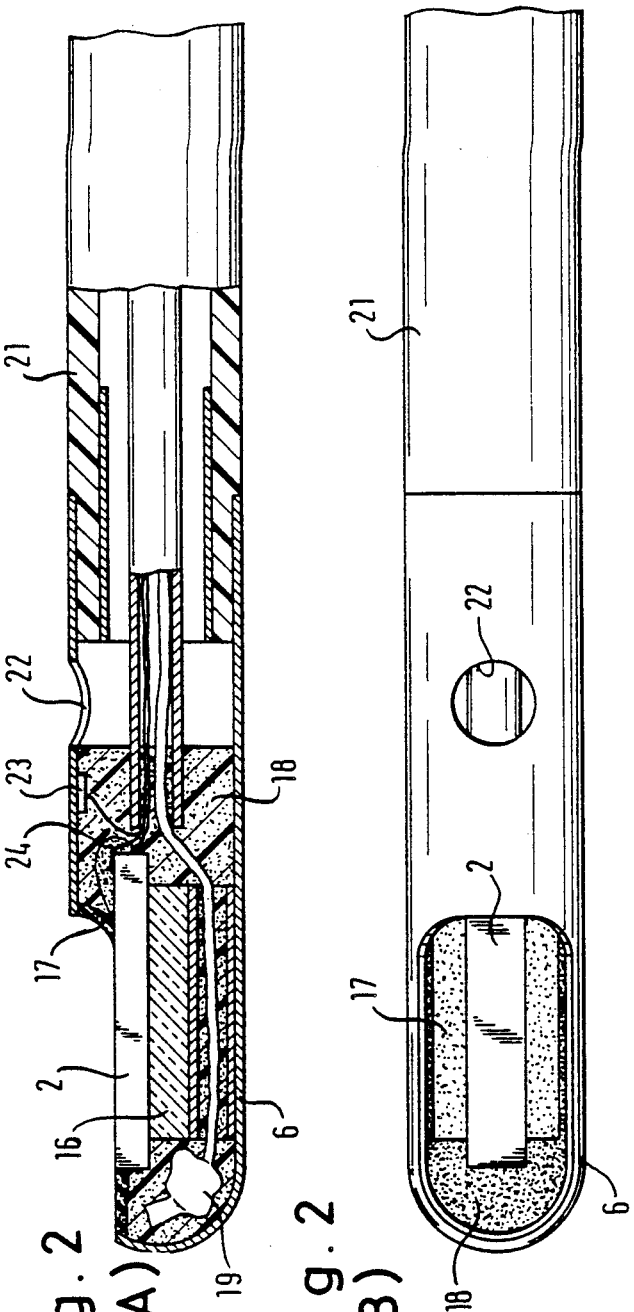

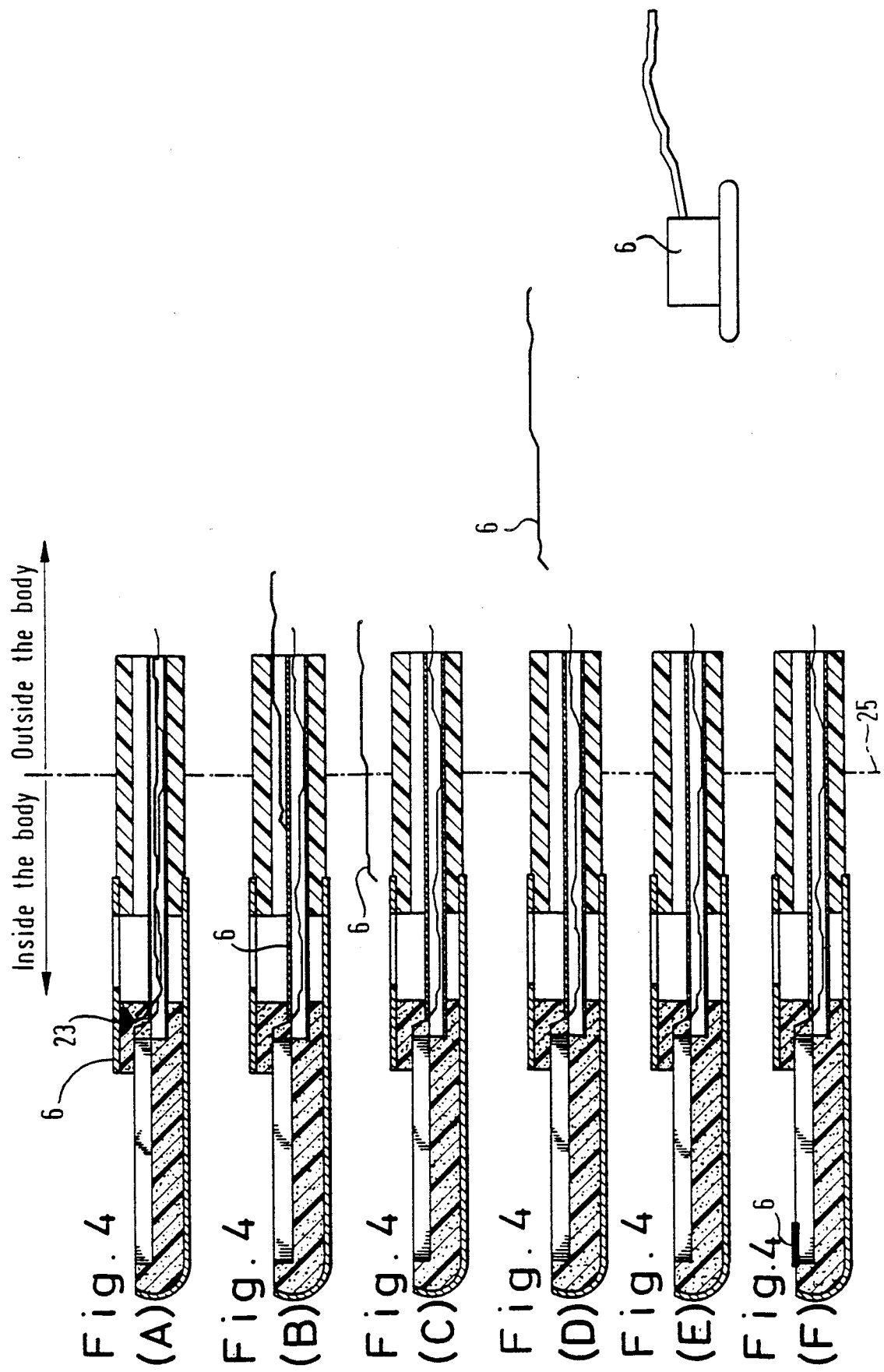

POLAROGRAPHIC-AMPEROMETRIC THREE-ELECTRODE SENSOR

FIELD AND BACKGROUND OF THE INVENTION

The present invention relates to a potentiostatically operable, polarographic-amperometric three-electrode sensor, in particular for biomedical use, wherein a working electrode and a reference electrode are covered by a layer receiving an electrolyte or an electrolyte-containing layer and the latter is separated from the medium to be measured by a semipermeable membrane.

U.S. Pat. No. 4,492,622 = EP-Al-0 149 693 describes a Clark cell wherein two electrodes extending through an insulating body having surface electrodes at their front end, namely a working electrode in the form of a thin wire (cathode) and a reference electrode surrounding the working electrode (anode). The front surfaces of both electrodes are covered by a hydrophilic polymer layer activated by an electrolyte which passes through fine holes in a covering hydrophobic membrane. The two electrodes thus are in direct galvanic contact with the physiological fluid whose specific properties, e.g. oxygen content (pO$_2$) or glucose content shall be determined.

This known two-electrode system has various practical advantages, in particular it can be stored over a long period of time although it is available relatively rapidly and simply for use. However, certain difficulties arise from the limited lifetime of the silver anode which on the surface converts to silver chloride, in particular when partial pressures of oxygen are measured.

Polarographic oxygen sensors in the form of three-electrode systems have also been known for a long time which additionally are equipped with a counter electrode as third electrode, and which are operated potentiostatically to prevent polarization of the counter electrode. A silver/silver chloride electrode is used as a reference electrode. The chloride concentration can be maintained constant, and due to the constancy of the reference potential the polarographic current will depend only on the concentration of oxygen (c.f., for example, the essay by I. Fatt, "Polarographic Oxygen Sensor", CRC-Press, Inc., Cleveland, Ohio, U.S.A. 1985, pages 1–7). In other words: By means of the reference electrode, the voltage drop at the working electrode is kept constant under the condition that the voltage drop at the reference/liquid interface is kept constant by the nearly constant concentration of chloride ions. The current will flow between the working electrode and the counter electrode, at which surface oxidation must take place. This oxidation of oxidizable components in the liquid may be described by the reaction:

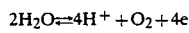

$$2H_2O \rightleftharpoons 4H^+ + O_2 + 4e$$

In connection with the sensors in question which have been known so far and which are used for biomedical measurements as intravasal or transcutaneous sensors, all electrodes also in three-electrode system of U.S. Pat. No. 4,492,622 are protected against the surrounding physiological medium by a membrane which is permeable preferably to the gases to be measured, e.g. oxygen. Also the electrodes and the functional electrolytes are separated from the enviroment to be measured by a membrane permeable to gases and impermeable to liquids. While in three-electrode systems—as suggested by Severinghaus as early as in 1970—by potentiostatic operation by means of an operational amplifier whose output is connected to the counter electrode (anode) and whose one input (minus input) is connected to the reference electrode, a defined potential can be obtained at the working electrode (cathode) so that contamination of the anode is substantially avoided, there is a problem: In the Severinghaus concept a membrane must be used over all the electrodes, including the electrolyte. In addition, such sensors are much more expensive, in particular when very small structures are intended to be used like microelectrodes which shall be fabricated with planar techniques as CMOS or bipolar structures by integration with the required interface electronics; (viz. W. Sansen, "Fabrication of Voltammetric Sensors with Planar Techniques", Conference paper "International Conference on Solid-State Sensors and Actuators:, TRANSDUCERS 85, IEEE Transactions, pages 344, 345).

SUMMARY AND OBJECTS OF THE INVENTION

Thus it is the object of the present invention to provide a potentiostatically operable, polarographic-amperometric three-electrode sensor, in particular with very small spatial dimensions for biomedical applications which is comparably simple in fabrication, in particular as a microsensor with integrated planar techniques.

According to the invention a potentiostatically operable, polarographic-amperometric three-electrode sensor of the afore-mentioned type is characterized in that the counter electrode is an external electrode.

It has been known that to a three-electrode system of the present invention the potentiostatic method proposed by Severinghaus can be applied successfully also when the working electrode and the reference electrode are located within the electrochemical cell, that means covered by an electrolyte layer and a gas permeable membrane, while the counter electrode is provided, for example, in the form of an external metal layer surrounding the system of the two first-mentioned electrodes. In the latter case the metal layer of the counter electrode surrounding the electrochemical cell proper also has the effect of a very much desired screening against external interference fields.

Between the working electrode and the external counter electrode there flows a relatively small current of the order of <0.1 μA so that in the case of intravasal use as a biomedical sensor there is no danger for the patient.

The sensor can be fabricated in the known fashion in the form of a chip with planar technique wherein the reference electrode which has a large surface and the working electrode located therebetween are provided on the main face of the chip.

The counter electrode can be provided as a metal coating at least partly surrounding the sensor body (chip), that means like a housing made of non corrosive metals, like thin stainless steel, optionally of platinum, gold, silver or titanium, depending on the use for which the sensor is intended. The counter electrode can also be a metal component, somewhere attached to or in the sensor.

For the coating of the counter electrode, also other electrically conductive materials can be used, in particular polymeric plastic materials like polycarbazolyte, polypyrrol, and elastomers enriched with gold, silver or carbon.

For specific cases of application, e.g. as transcutaneous sensor, a different external metal electrode can be provided as the counter electrode which is fixed on the skin of a patient at a different location of the body, for example an ECG electrode.

BRIEF DESCRIPTION OF THE DRAWINGS

The invention and further advantageous details are explained below in more detail on the basis of an embodiment by way of example with reference to the drawing in which:

FIGS. 2(A) and 2(B) depict an embodiment of an intravasally used sensor showing features of the present invention;

FIG. 3(A) is a known oxygen sensor designed as a semiconductor chip for which the present invention is advantageously suited, in particular and as an example in the mode of application according to FIG. 2; and FIGS. 4(A)-(F) depict schematically several modes for application of the counter electrode in similar configurational assemblies.

DETAILED DESCRIPTION OF THE PREFERRED EMBODIMENTS

Figure 1:
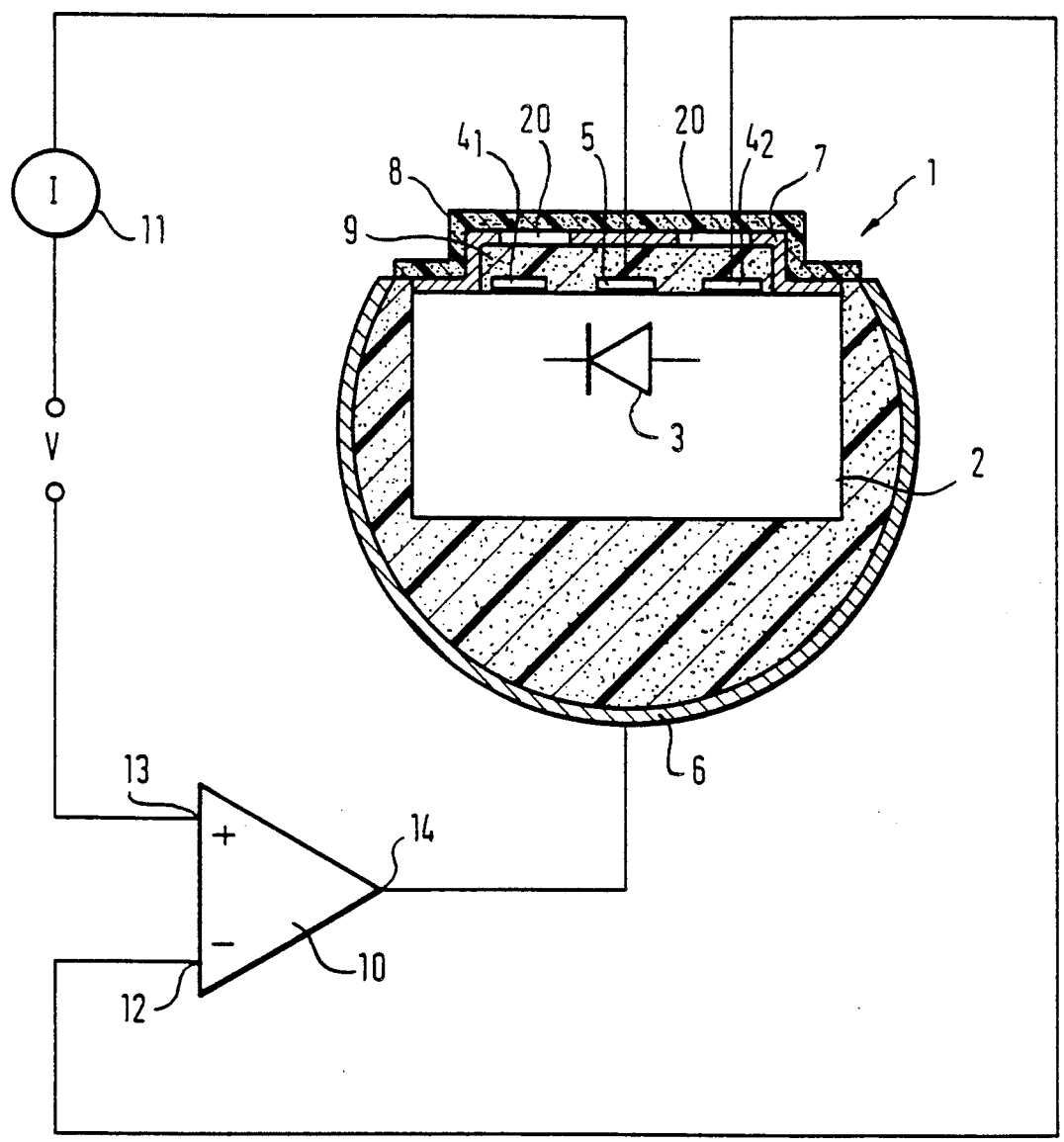
FIG. 1 is the section through a potentiostatically operable, polarographic-amperometric three-electrode sensor, in a principle illustration.

FIG. 1 shows the basic principle of a potentiostatically operable, polarographic-amperometric three-electrode sensor 1, wherein on a chip body or chip substrate on the surface thereof a reference electrode $4_1$, $4_2$ is provided in the form of a ring or two strips according to the planar technique known in connection with the fabrication of integrated circuits. In the center between the two partial areas $4_1$ and $4_2$, respectively, of the reference electrode there is a working electrode 5. In the manner known from U.S. Pat. No. 4,492,622, the reference electrode $4_1$, $4_2$ and the working electrode 5 which are disposed in the same plane can be covered by a hydrophilic polymeric layer or a hydrogel which is impregnated for receiving an electrolyte suited for the respective purpose of measuring, e.g. which is activated by the part of the body fluid in which the measurement shall be made. In the fashion described in the cited U.S. patent the hydrophilic polymeric layer 9 can be covered by a hydrophobic membrane 7 and this membrane in turn by a gas permeable membrane 8 selected under specific measuring conditions serving as a blockage to proteins and letting the electrolyte pass.

The hydrophobic membrane 7 is provided with several holes 20 at a sufficient distance from the working electrode 5 through which holes the hydrophilic polymer layer can be activated by penetration of the electrolyte. The chip-like sensor 1 moreover is provided, as is known, with an integrated temperature sensor 3 which in fact is important for the correction of the measuring results but which is inessential in conjunction with the present invention.

As an essential element of the invention, the two-electrode sensor system below the membrane 7 is completed by an external counter electrode 6 to a three-electrode system. For example in the manner illustrated in FIG. 1, the counter electrode 6 is an external metal coating surrounding the body 2 of the chip; in this way it acts as counter electrode and simultaneously as a screen. When it is used in particular as $pO_2$ sensor, oxygen develops predominantly on immersion into the medium to be measured only at the outside of the counter electrode 6, i.e. below the membrane 7 there will be no disturbing $O_2$ development despite a very low current density at the outside.

As shown in FIG. 1 and known per se, the working electrode 5 is held at a defined potential value in that the operating voltage between the counter electrode 6 and the working electrode 5 is supplied by separation by means of an operational amplifier 10 to whose output the counter electrode 6 is applied and to whose plus input the supply voltage is applied, as is known. The reference electrode $4_1$, $4_2$ is connected to the minus-input of the operational amplifier 10. The polarographic current which flows through the working electrode 5 is measured by a current meter 11 and is evaluated as a measure e.g. for the oxygen concentration or the glucose concentration.

FIG. 2 shows an embodiment of an intravasal $pO_2$ sensor the structure of which is known per se, wherein the $pO_2$ sensor chip 2 only shown schematically is exposed at the front end of a sensor tube 21 and is based on a glass substrate 16, fixed by an epoxy resin mass 18, but sealingly supported by a silicon rubber embedding 17. A reinforcing wire or cable is thickened at the end projecting beyond the sensor chip 2 and serves the axial reinforcement of the total structure as considerable traction forces can be applied to the sensor tube 21, in particular to its front end at which the $pO_2$ sensor chip 2 is provided, for example, when it is used for measurements in the interior of the heart.

In the embodiment illustrated in FIG. 2 the counter electrode 6 can be a thin metallic coating on the outside of the front end of the whole sensor system that is electrically connected via a contact area 23, adhered by silver-epoxide bonding to a multi wire cable 24 for connection with the electronic circuitry, i.e. with the output of operational amplifier 10 in this case as shown in FIG. 1. It would also be possible to place the counter electrode 6 in the inner space or external but in connection with the inner space of the sensor arrangement around which flows the measuring liquid (e.g. blood) via an opening 22, and then to provide it e.g. in the form of a metal wire or a flexible tube receiving the measuring conduits and the reinforcement 19.

FIG. 3 shows an embodiment wherein the sensor chip has been fabricated according to the integrated planar technique. The shown chip body has e.g. a length $l=3.7$ mm and a width $b=0.7$ mm. The sections of the reference electrode in the form of surfaces in turn are designated $4_1$, $4_2$. There can be provided a triple layer arrangement, e.g. of Ti, Au or Ti, Pt or Ti, Pt, and Au, wherein Ti may be replaced by other metals from the transition elements group like Zr, Ta, Mo, W, and so on with a total thickness of about 1.5 $\mu$m. The connecting area is designated $4_3$. The narrow strip of the working electrode 5 is contacted via the connection area $5_1$. The temperature sensor 3 shown only schematically is supplied with current via the connecting areas $3_1$, $3_2$, while a mass connection is designated 15. For fabricating the counter electrode 6 (not shown), the chip body 2 can be metallized at the underside or can be formed by a highly doped layer of good electrical conductivity.

It may be advantageous to cover the separate counter electrode 6 by a hydrophilic semipermeable polymer for some specific applications. The polymer will be impermeable to proteins avoiding the electric charged proteins to reach and to contaminate the surface of the counter electrode, i.e. by polarizing and blocking this surface.

With reference to FIG. 2, FIG. 4 explains several modes for a counter electrode configuration assembly. In FIG. 4(A), as in FIG. 2, the outside cover counter electrode 6 is contacted via a contact area 23.

In FIG. 4(B), the counter electrode is within the lumen of the liquid (blood) flow.

In FIG. 4(C), the counter electrode 6 is a wire electrode external to the catheter but in the body.

In FIG. 4(D), the counter electrode is external to the catheter but in conductive contact with the liquid to be measured, e.g. blood.

FIG. 4(E) shows the case where the counter electrode 6 is a body skin electrode, e.g. an ECG electrode.

Finally, FIG. 4(F) shows the case where the counter electrode 6 is a surface electrode integrated on the chip 2, however, outside of the two or three membrane configuration as shown in FIG. 1.

In FIG. 4, a dotted line 25 shows which part of the catheter is inside the body and which part is outside the body.

We claim:

1. A potentistatically operable, polarographic-amperometric three-electrode sensor for biomedical use comprising a working electrode and a reference electrode covered with a hydrophilic layer impregnated for electrolyte reception, a hydrophobic membrane covering said hydrophilic layer, a gas permeable membrane covering the hydrophobic membrane, said gas permeable membrane being permeable to electrolyte but impermeable to proteins, a plurality of holes provided through the said hydrophobic membrane, said holes communicating with said hydrophilic layer to thereby provide passage for activating electrolyte from the surface of the sensor to the hydrophilic layer and an external counter electrode at least partially surrounding the sensor.

2. The sensor of claim 1 wherein the counter electrode is a metal layer.

3. The sensor of claim 1 wherein the counter electrode is metal which makes direct contact with the medium being measured by the sensor.

4. The sensor of claim 1 wherein the counter electrode is an ECG electrode.

5. The sensor of claim 1 wherein the counter electrode is a metal coating provided on the sensor biochemically inert to blood.

6. The sensor of claim 1 wherein the counter electrode is an electrically conductive plastic.

7. The sensor of claim 1 wherein the externally positioned counter electrode is a surface electrode.

8. The sensor of claim 1 wherein the sensor is tubular in shape and is constructed to permit insertion into a body cavity, the outer surface of said sensor being at least partially formed by an electrically conductive coating acting as the counter electrode.

* * * * *